United States Patent
Balbierz

Patent Number: 5,814,021
Date of Patent: Sep. 29, 1998

[54] ADJUSTABLE SECURING WINGS

[75] Inventor: Daniel J. Balbierz, Redwood City, Calif.

[73] Assignee: Johnson & Johnson Medical, Inc., Arlington, Tex.

[21] Appl. No.: 773,975

[22] Filed: Dec. 26, 1996

[51] Int. Cl.$^6$ ..................................................... A61M 5/32
[52] U.S. Cl. .................. 604/174; 128/888; 128/DIG. 6; 128/DIG. 26
[58] Field of Search ...................... 604/174, 175, 604/177, 178, 165, 160, 161, 166; 128/DIG. 26

[56] References Cited

U.S. PATENT DOCUMENTS

| | | | |
|---|---|---|---|
| 3,537,451 | 11/1970 | Beck et al. | 604/165 |
| 4,170,995 | 10/1979 | Levine et al. . | |
| 4,177,809 | 12/1979 | Moorehead | 604/165 |
| 4,192,304 | 3/1980 | Millet | 604/177 X |
| 4,419,094 | 12/1983 | Patel . | |
| 4,449,975 | 5/1984 | Perry . | |
| 4,585,443 | 4/1986 | Kaufman . | |
| 4,792,330 | 12/1988 | Lazarus et al. . | |
| 4,869,719 | 9/1989 | Hogan . | |
| 4,995,872 | 2/1991 | Ferrara . | |
| 5,084,026 | 1/1992 | Shapiro | 604/174 |
| 5,192,273 | 3/1993 | Bierman et al. . | |
| 5,215,530 | 6/1993 | Hogan . | |
| 5,292,312 | 3/1994 | Delk et al. . | |
| 5,314,411 | 5/1994 | Bierman et al. . | |
| 5,380,293 | 1/1995 | Grant | 604/177 |
| 5,484,420 | 1/1996 | Russo . | |

*Primary Examiner*—Michael A. Brown
*Attorney, Agent, or Firm*—Blakely, Sokoloff, Taylor & Zafman

[57] ABSTRACT

The invention relates to an adjustable anchoring device to retain a catheter at a desired location inside a patient. The anchoring device includes a securing member with a body portion having an opening extending through the tubular body portion. The opening has a first dimension adapted to retain the catheter by frictionally engaging the catheter. The body portion of the securing member is dilatable to have an opening with a second dimension such that the securing member can slidably move about the catheter. The invention also relates to an anchoring device with a dilator member portion with a forward end wherein the forward end is adapted to detachably mate with the securing member through a portion of the opening of the securing member and to dilate the tubular body portion of the securing member from having an opening with the first dimension to have an opening with the second dimension.

34 Claims, 6 Drawing Sheets

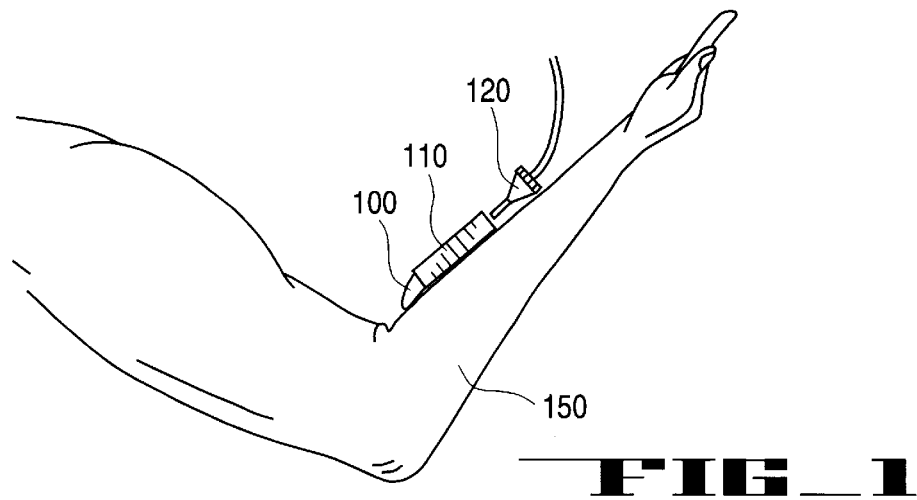
FIG_1
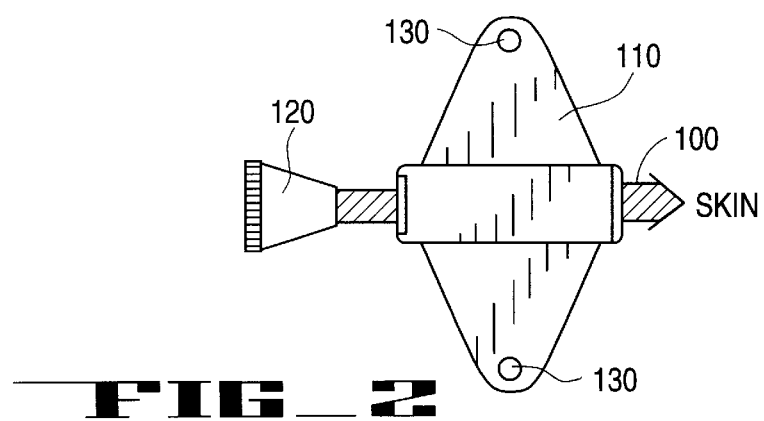
FIG_2
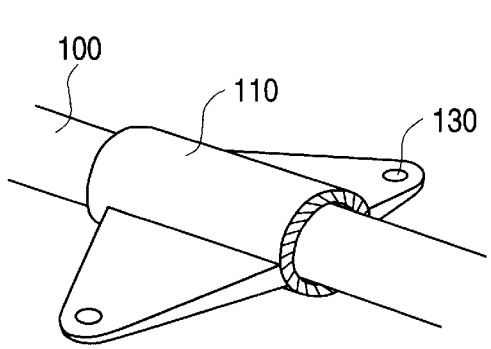
FIG_3
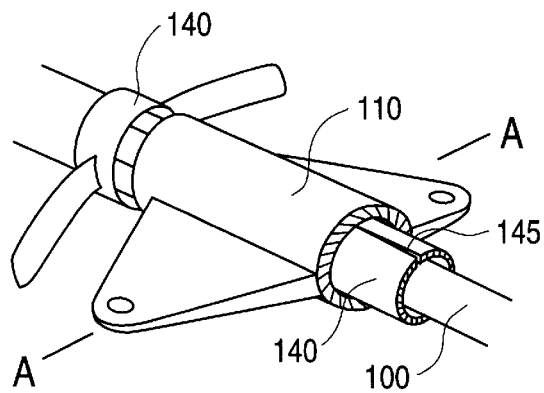
FIG_4

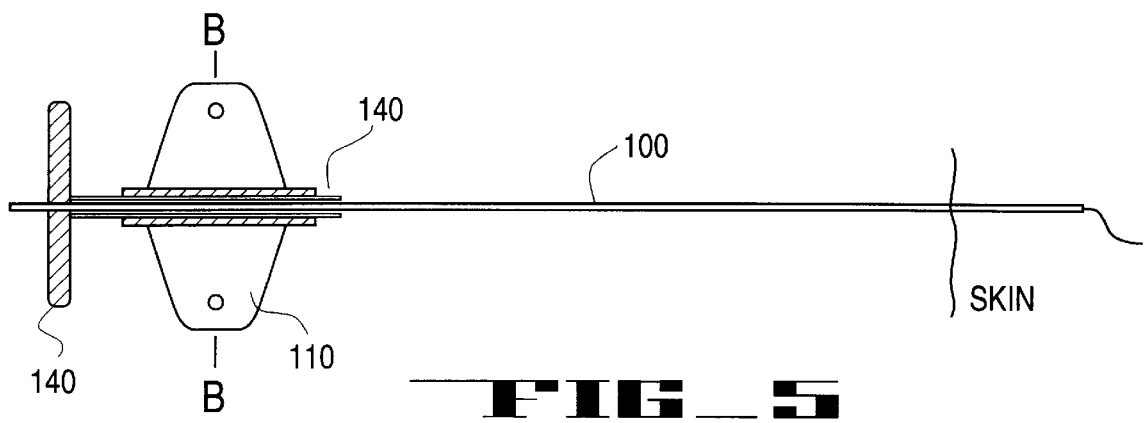
FIG_5
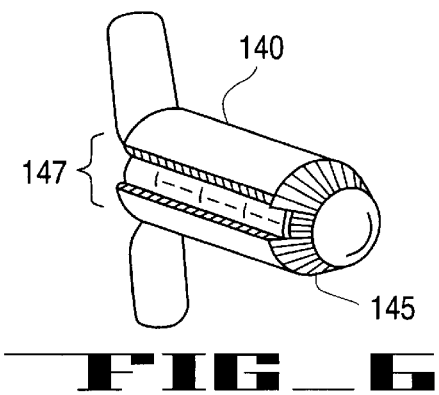
FIG_6
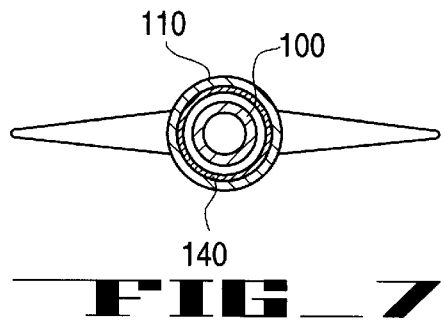
FIG_7
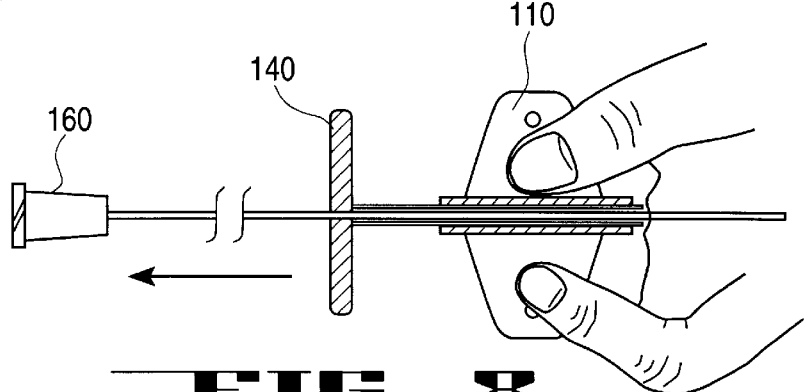
FIG_8
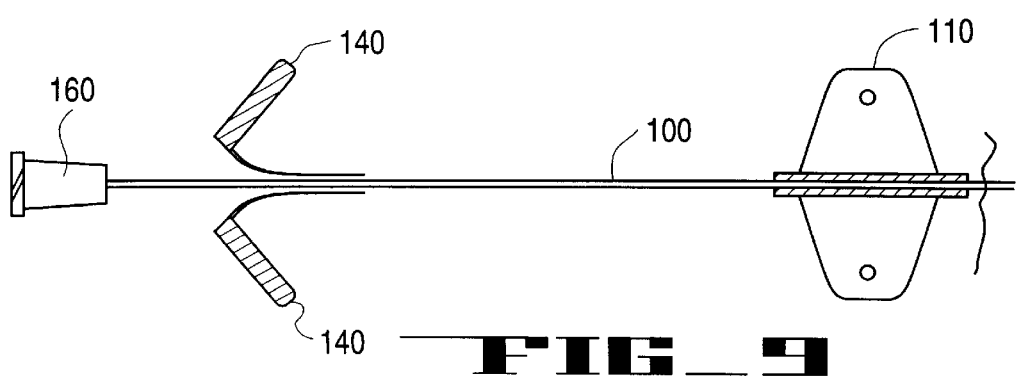
FIG_9

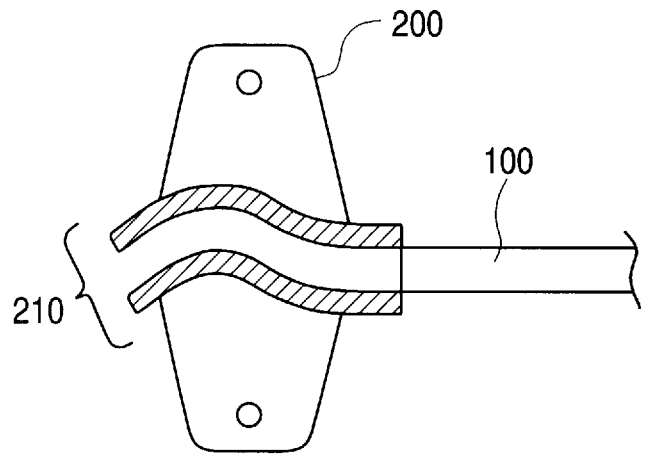
FIG_10
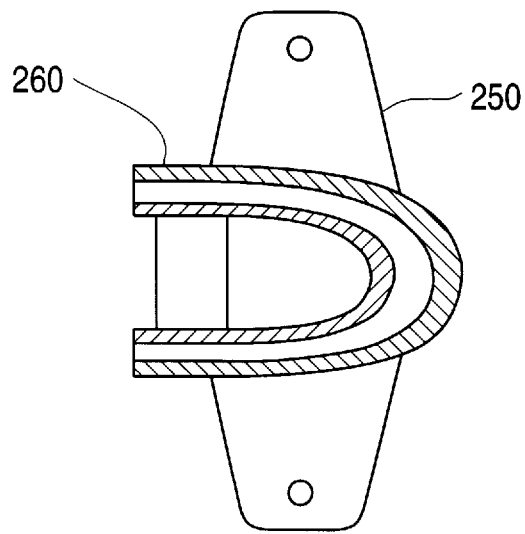
FIG_11

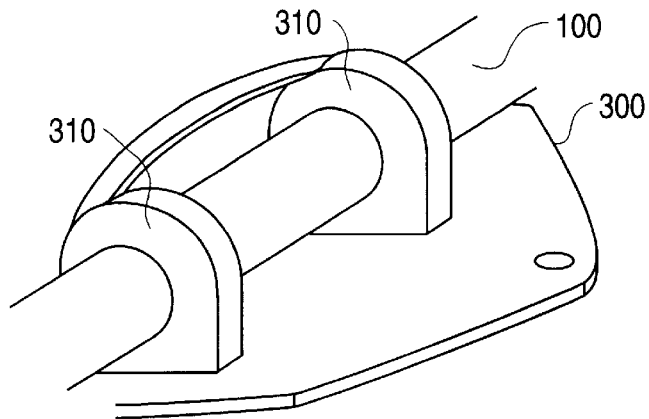
FIG_12
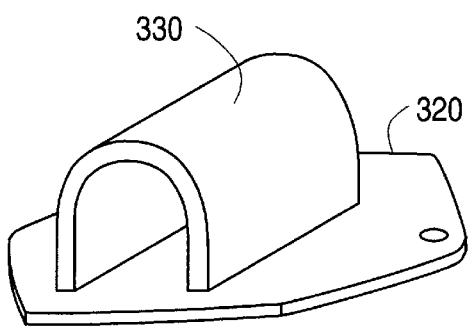
FIG_13
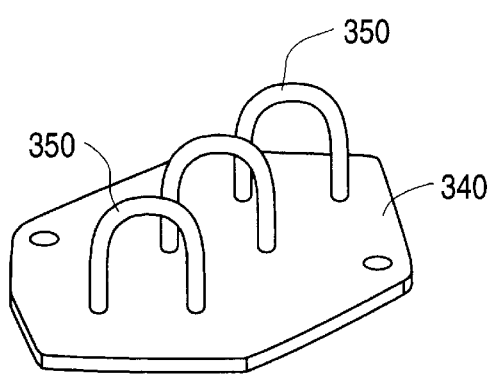
FIG_14
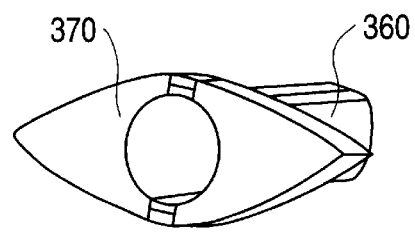
FIG_15

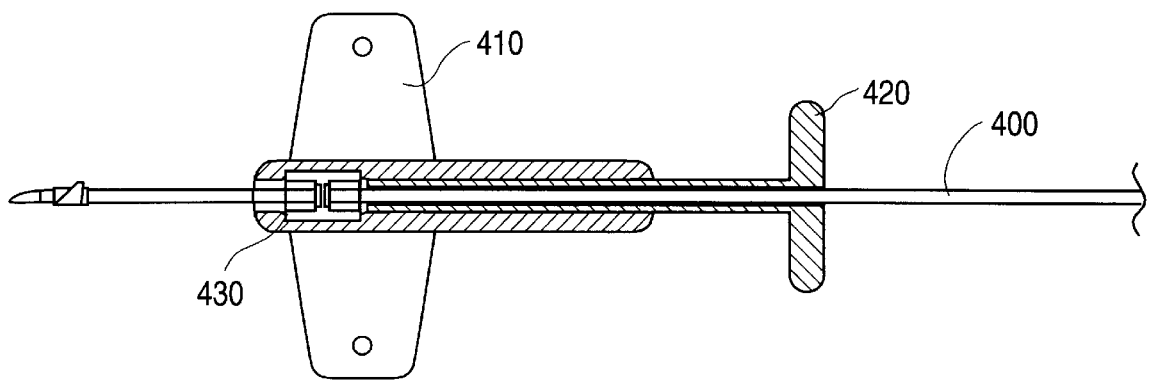
FIG_16
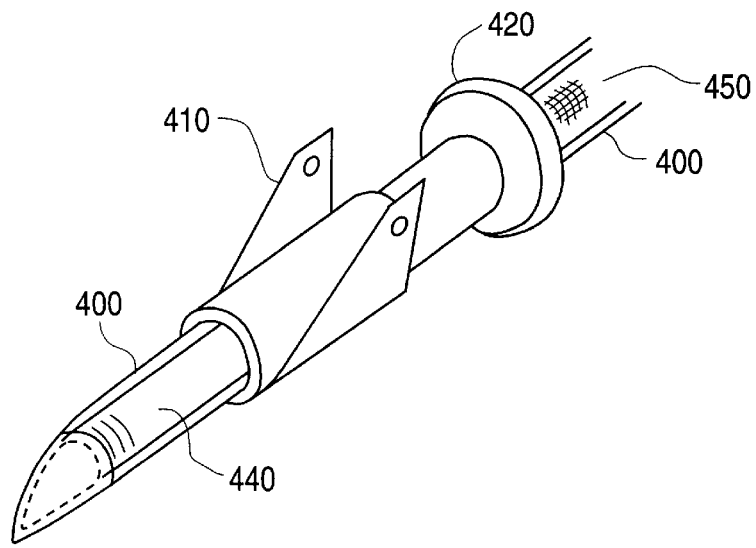
FIG_17

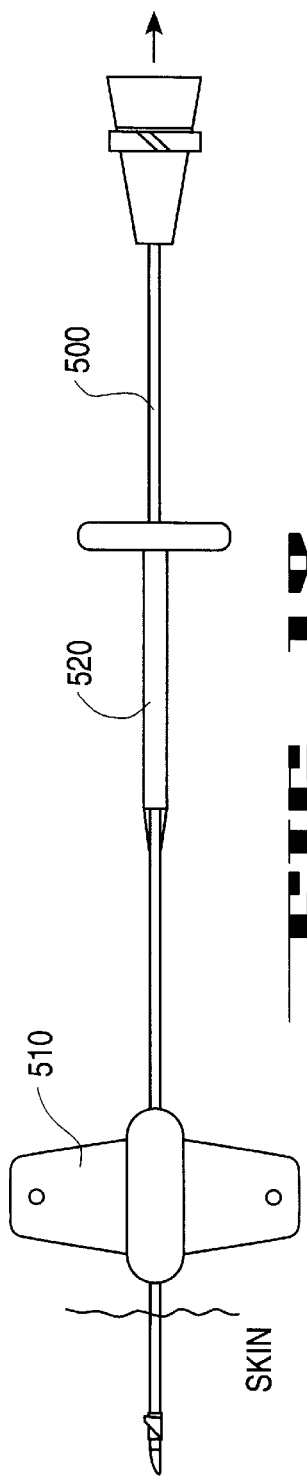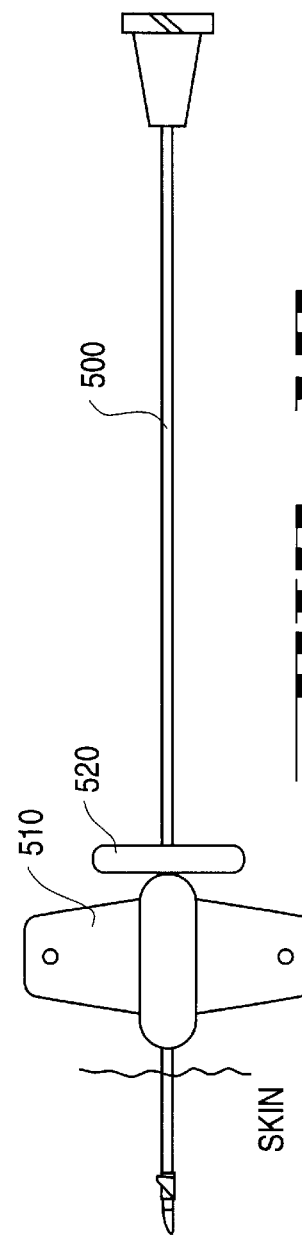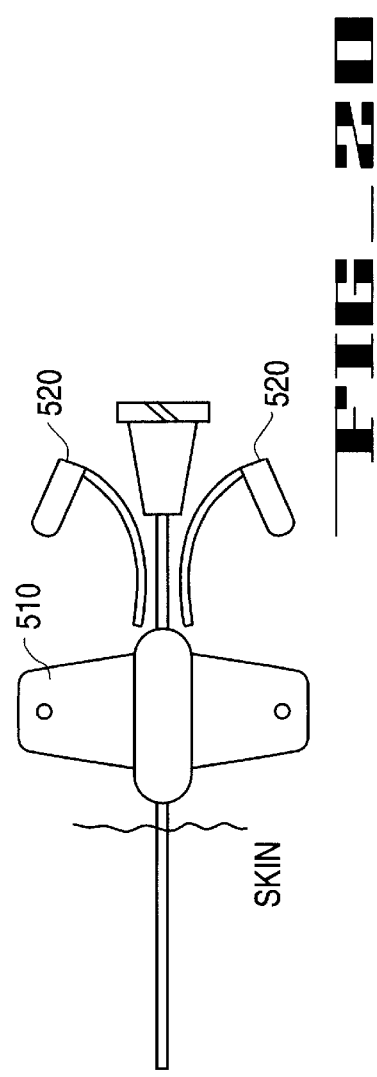

ADJUSTABLE SECURING WINGS

BACKGROUND OF THE INVENTION

1. Field of the Invention

The invention relates to percutaneous catheters and more specifically to anchoring devices to secure percutaneous catheters at a desired location in a patient's body.

2. Description of Related Art

Percutaneous catheters are commonly used in medical applications to deliver or remove fluids from a patient's body. It is very common in the treatment of patients to utilize intravenous catheters to introduce certain fluids directly into the bloodstream of the patients. It is also common to utilize catheterization to bypass blocked passage between organs. For example, when the passage between a kidney and the bladder is blocked, accepted treatment can be provided by catheterization of the kidney to drain urine.

In general, a catheter consists of a soft tube, or cannula, having an opening, or lumen, extending through the cannula. Placing a catheter usually involves introducing an introducer sheath enveloped around a needle, the introducer sheath having an outside diameter slightly larger than the needle, into the patient at the desired location, and then removing the needle. The catheter is then introduced into the patient through the introducer. In the case of an intravenous catheter, the infused fluid flows directly through the catheter into the vein in which the catheter is introduced. In the case of a urinary drainage catheter, the urine is drained directly from the kidney to a dispensary.

In as much as catheters have different uses, catheters also have different lengths. For intravenous catheters, for example, there exists several various lengths of catheters including short intravenous catheters that are placed peripherally, for example, in the hand, midline catheters that are fed approximately six to eight inches into a vein, for example, from the hand to the upper arm where the vein is bigger and better hemodilution and blood flow is achieved, and central venous catheters of significant length that may be placed peripherally, i.e., in the arm, and fed, for example, to the superior vena cava. Regardless of the length, it is desired to secure the catheter so that it maintains its position in the body. Catheter positioning in the patient's body is important, particularly in determining the concentration and toxicity of fluid added to the body. To ensure that the catheter maintains its position, the catheter should be anchored to the exterior body of a patient, and ideally it should be anchored as closely as possible to the entry site or junction of the catheter to provide less opportunity for the catheter to be repositioned.

Common securing devices include tape-down or lock-down wings fixedly attached to the catheter cannula. The fixed-location catheter lock-down wings work well if the full length of the catheter cannula is placed in the patient so that the wings are secured at the junction. A problem, however, arises when the decision is made to shorten the placement of the catheter in the patient so that excess catheter material separates the lock-down wings from the introduction site or junction. If the wings are anchored to the patient at a position that is too far away from the insertion site, migration or pistoning of the catheter cannula can occur. One way to get around this is to cut the catheter cannula to length before insertion of the catheter into the body. Because most catheters include a hub at their distal end, the only convenient end to cut away is the introductory end. However, catheter cannulas are generally constructed with a tapered tip at the introductory end to make insertion easier, i.e., less traumatic, to the patient. If the tapered tip is removed, for example by clipping a section of the catheter away, such patient considerations are ignored. Further, if the shortened estimate turns out to be incorrect, the physician or nurse still has excess catheter cannula material that must be dealt with. Another way to deal with the excess cannula material that extends from the junction, whether or not the catheter has been shortened, is to coil the excess catheter cannula material around the securing wings before the wings are secured to the patient. This method allows the securing device to be anchored at the junction, but creates an awkward and bulky device.

Adjustable anchoring devices have been introduced that allow the device to be positioned at the catheter junction once the catheter is placed. However, these devices are either bulky or difficult to effectively install at the junction site. One adjustable anchoring device is a two-piece device wherein a flexible first piece with a split along its bottom portion fits over the cannula adjacent to the junction, and a second rigid piece snaps over the first piece to compress the first piece to the cannula so that the catheter device cannot move. The entire apparatus is then sutured or taped to the skin. A problem with this type of device is that it is a two-piece device that must be sized and fit on the catheter cannula at the junction. The placement of the securing device must be done in an artful manner so as not to disturb the patient or lose the distinct pieces. Further, the second rigid piece makes the device bulky.

Another type of adjustable anchoring device is compressing an eyelet, two-piece squeeze fit fastening device. This device utilizes at least one cylindrical eyelet that fits around the catheter and inside a two-piece fastening device mounted on the catheter cannula. When the fastening device is forced together, the eyelet is compressed to apply frictional pressure to the catheter. This securing device involves at least three pieces that may be easily misplaced and it is difficult to manipulate and install the fastening device at the junction.

What is needed is an adjustable anchoring device that is easy to install at the junction of a patient and is not bulky or cumbersome.

SUMMARY OF THE INVENTION

An adjustable anchoring device to retain a catheter at a desired location inside a patient is disclosed. The anchoring device includes a securing member with a tubular body portion and an opening extending through the tubular body portion. The opening of the tubular body portion has a first dimension that is adapted to retain the catheter by frictionally engaging the catheter. The body portion is also dilatable to form an opening with a second dimension such that the securing member can slidably move about the catheter. The anchoring device is intended to secure any of the various types of catheters, including, but not limited to, vascular, neurological, and urinary drainage catheters.

A dilator member to dilate the tubular body portion of the securing member from having an opening with the first dimension to an opening with the larger second dimension is also disclosed. The dilator member includes a forward end that is adapted to detachably mate with the securing member through a portion of the opening of the securing member. The mating dilates the body portion of the securing member from an opening with the first dimension to an opening with the second dimension. In the mated position, the dilator member and the securing member are adapted to slidably move about the catheter to easily position the catheter at the desired location, e.g., the junction.

Additional features and benefits of the invention will become apparent from the detailed description, figures, and claims set forth below.

BRIEF DESCRIPTION OF THE DRAWINGS

FIG. 1 is a planar side view of an intravenous catheter in place in the arm of a patient wherein the intravenous catheter is secured by the anchoring device of the invention.

FIG. 2 is a planar top view of the anchoring device of the invention used to secure an intravenous catheter in a patient.

FIG. 3 is a perspective side view of the anchoring device of the invention securing a catheter.

FIG. 4 is a perspective side view of the anchoring device of the invention including a securing member that is dilated by a dilator member to be slidably movable about the catheter.

FIG. 5 is a planar top view of the anchoring device of the invention taken through line A—A of FIG. 4 wherein the securing member is dilated by a dilator member to be slidably movable about the catheter.

FIG. 6 illustrates a perspective side view of the dilator member portion of the anchoring device of the invention.

FIG. 7 is a cross-sectional side view of the anchoring device of the invention taken through line B—B of FIG. 5.

FIGS. 8 and 9 illustrate the method of removal of the dilator member from the securing member. FIG. 8 illustrates that the dilator member is separated from the securing member. FIG. 9 illustrates that the dilator member is broken and removed from the catheter.

FIG. 10 is a planar top view of a securing member of the anchoring device of the invention wherein the securing member has a tubular body portion that is curved.

FIG. 11 is a planar top view of a securing member of the anchoring device of the invention wherein the securing member has a tubular body portion that is a complete curve or "U".

FIG. 12 is a perspective side view of a securing member of the anchoring device of the invention wherein the securing member includes a pair of annularly shaped portions.

FIG. 13 is a perspective side view of a securing member of the anchoring device of the invention wherein the securing member includes a substantially arcuately-shaped body portion.

FIG. 14 is a perspective side view of a securing member of the anchoring device of the invention wherein the securing member includes three substantially arcuately-shaped body portions.

FIG. 15 is a perspective side view of an embodiment of a dilator member portion of the invention.

FIG. 16 is a planar top view of the anchoring device of the invention used with an over-the-needle catheter device.

FIG. 17 illustrates a top perspective view of an embodiment of the anchoring device of the invention with a securing member with deformable clamping wings.

FIGS. 18–20 illustrate a method of installing the adjustable anchoring device of the invention wherein a portion of the dilator member portion is inserted into the patient to act like an introducer.

DETAILED DESCRIPTION OF THE INVENTION

The invention relates to an adjustable anchoring device to retain a catheter at a desired location inside a patient. The invention is described below with reference to the following drawings. In the following description, numerous specific details are set forth such as specific materials, configurations, and catheter types. It will be obvious, however, to one skilled in the art that these specific details need not be employed to practice the invention. In other instances, well-known materials or methods have not been described in detail in order to avoid unnecessarily obscuring the invention.

FIGS. 1–8 illustrate an embodiment of the anchoring device of the invention. FIG. 1 illustrates the anchoring device of the invention to secure an intravenous catheter. The embodiment shown in FIGS. 1–8, however, may be used with any type of catheter, including, but not limited to, intravenous catheters, neurological catheters, and urinary drainage catheters.

The invention relates to an adjustable anchoring device to retain a catheter at a desired location inside a patient. In the intravenous catheter example illustrated in FIG. 1, a catheter 100 is placed in a patient's arm 150 to a vein therein. Once the catheter cannula 100 is inserted to the desired length inside the patient, the anchoring device of the invention is positioned directly next to the junction (i.e., the injection site). The anchoring device of the invention includes a securing member 110. The securing member 110 has a tubular body portion with an opening extending through the tubular body. The opening of the securing member 110 has a diameter sized to retain the catheter cannula 100 by frictionally engaging the catheter cannula 100 such that the securing member 110 is not movable about the catheter cannula 100. This is best illustrated in the perspective view of FIG. 3 which illustrates the securing member 110 frictionally engaged to the catheter cannula 100. The diameter of the opening of the securing member 110 can also be sized slightly smaller than the catheter cannula 100 to impart a compressive force to the cannula 100, in addition to the frictional force. Once the securing member 110 is properly positioned at a desired location, the winged portions of the securing member 110 may be sutured or taped to the patient's skin.

FIGS. 1 and 2 illustrate an anchoring device with a securing member 110 situated at a desired location adjacent the catheter hub 120. To position the securing member 110, the anchoring device of the invention includes a dilator member 140. The dilator member 140 can slidably move about the catheter cannula 100. In other words, the dilator member 140 has an opening with a diameter larger than the catheter cannula 100. The dilator member 140 is adapted to mate with securing member 110 through a portion of the opening in the tubular body portion of securing member 110.

FIG. 4 illustrates a perspective view of the anchoring device of the invention about a catheter cannula 100. FIG. 4 shows a securing member 110 with an opening that has been dilated by dilator member 140 so that securing member 110 does not frictionally engage the catheter cannula 100. Instead, the entire anchoring device assembly, including the dilator member portion 140 and the securing member portion 110, collectively define an opening of sufficient diameter to move the anchoring device about the catheter cannula 100. The dilator member 140 has a score or slice 145 running along its length to allow the dilator member 140 to be divided into two pieces to facilitate its removal from the catheter once the securing member 110 is in place.

FIG. 5 illustrates a top, cross-sectional view of the anchoring device of the invention through lines A—A of FIG. 4. FIG. 5 shows a dilator member portion 140 that includes a tubular body portion having an opening extending through the body portion and a diameter of the opening greater than the outside diameter of the catheter cannula 100.

FIG. 6 illustrates a perspective side view of the dilator member 140 of the invention. The dilator member 140 includes a substantially tubular body portion with an opening extending the length of the body portion. The body portion is made of a durable material like plastics such as polyurethane, polyethylene, TEFLON® (produced by E. I. DuPont de Nemours and Company, Wilmington, Del.), polypropylene, and polyvinyl chloride. The body portion of the embodiment shown in FIG. 6, includes a tapered portion 145 to ease insertion and mating with securing member 110. The dilator member 140 further includes a section of reduced wall thickness or scored (e.g., sliced with a blade) section 147 on opposing sides of the dilator member 140. The reduced thickness portions allow the dilator member to be divided into two pieces to remove the dilator member 140 from the catheter once the securing member 110 is in place.

FIG. 7 illustrates a cross-sectional view of the adjustable anchoring device of the invention taken through line B—B of FIG. 5. In FIG. 7, the anchoring device includes a securing member 110 with an opening dilated by dilator member 140 to expand the opening of the anchoring device such that the anchoring device can freely move about the catheter cannula 100 and be adjusted at any desired location.

Once the anchoring device, including the dilator member 140 and the securing member 110 is placed in the desired location about the catheter and in relation to the patient's body, the dilator member portion 140 is removed and the tubular body portion of the securing member 110 assumes a diameter that frictionally engages the catheter cannula 100. The opening in the tubular body portion of the securing member 110 is sized to frictionally engage the catheter cannula 100 so that the securing member 110 is not movable about the cannula 100. Thus, catheter cannulas of various sizes will have anchoring devices, including securing members with body portions of various diameters to securely engage the catheters by frictional gripping force. The invention also contemplates that the opening in the tubular body portion may be sized slightly smaller than the outside diameter of the catheter cannula 100. In this manner, the securing member 110 compressively as well as frictionally engages the cannula 100.

An important property of the securing member 110 is that it is dilatable and will return to its memorized, properly sized diameter once the dilator member 140 is removed. Suitable elastomeric materials for constructing the tubular body portion of the securing member so that it is dilatable but will return, in its non-dilated state, to frictionally or frictionally and compressively engage the catheter include, but are not limited to, silicone, polyurethane, latex, polyvinyl chloride, KRATON® (produced by Shell Oil Company, Houston, Tex.), isoprene, SANTOPRENE® (produced by Monsanto Company, St. Louis, Mo.), and HYTREL® (produced by E. I. DuPont de Nemours, Wilmington, Del.).

FIGS. 8 and 9 illustrate the removal of the dilator member 140 from the securing member 110 once the securing member 110 is placed in the desired location on the catheter 100. FIG. 8 demonstrates that the securing member 110 is held firmly in place by hand or other means, including sutures, tape, etc., and the dilator member 140 is advanced away from the securing member 110. Once the dilator member 140 is away from the securing member 110, the securing member 110 frictionally or frictionally and compressively engages the cannula 100. Also, while pulling the dilator member 140 away from the securing member 110, the dilator member is divided and peeled away from the catheter. As noted above, ways that the dilator member 140 may be easily divided include scoring or slicing opposing side walls or constructing the dilator member 140 portion with opposing sides of reduced wall thickness, the division occurring along the portions 147 with reduced wall thickness, and then pulling the walls apart by hand.

FIGS. 8 and 9 describe an embodiment wherein the dilator member 140 is removed from the catheter once the securing member 110 is properly placed. The invention contemplates also that the dilator member may remain on the catheter and used for catheter reinforcement or kink resistance or the like.

FIGS. 10 and 11 illustrate different embodiments for the securing member portion of the anchoring device of the invention. FIG. 10 illustrates a securing member 200 that includes a tubular body portion 210 that is curved. The curvature of the tubular body portion 210 of the securing member 200 provides additional gripping support to securely hold the catheter cannula and can also guide the catheter into a direction different than the direction the catheter enters the securing member 110. The invention contemplates that a dilator member is similarly shaped so as to dilate, if necessary, the entire curved body portion 210 of the securing member 200. Similarly, FIG. 11 illustrates an embodiment of the anchoring device with a securing member 250 including a tubular body portion 260 that is completely curved. This allows an IV catheter, for example, to go into a patient at an angle 180° relative to the direction of the incoming IV drip line. Again, the invention contemplates that, if necessary, a dilator member portion will dilate the entire curved body portion 260 of the securing member 250.

FIG. 12 illustrates another embodiment of the securing member portion of the invention. FIG. 12 presents a securing member 300 with a pair of dilatible annularly shaped portions or rings 310 that surround the catheter cannula 100. In this embodiment, to dilate the securing member 300, a dilator member portion must dilate each securing wing 310.

FIGS. 13 and 14 illustrate other embodiments of the securing member of the invention. FIGS. 13 and 14 present securing member portions wherein the securing device is a non-tubular section or sections. The securing member 320 of FIG. 13 includes an arcuately-shaped or arched body 330 that engages a catheter cannula. The opening in the arch portion 330 frictionally or frictionally and compressively engages the cannula. FIG. 14 illustrates a securing member 340 that includes a plurality, in this case, three, arcuately-shaped portions 350 that are each dilatible and that frictionally or frictionally and compressively engage the catheter cannula.

FIG. 15 illustrates a second embodiment of the dilator member portion of the anchoring device of the invention. In FIG. 15, the dilator member 360 has a split collar 370 to facilitate the division of the dilator member 360. In FIG. 15, opposing wings of the collar portion 370 are pulled apart while the dilator member 360 is separated from the securing member.

The invention further contemplates that the securing member and optionally the dilator member are pre-loaded on the catheter body. The pre-loaded embodiment is particularly useful wherein the opening or openings in the securing member portion are sized slightly smaller than the catheter cannula. The pre-loaded embodiment also eliminates the possible misplacement of the components of the anchoring device and facilitates the simple installation of the anchoring device. Of course, the invention also contemplates an anchoring device that is not pre-loaded, but that is installed on the catheter once the catheter is placed in a patient. Further, because the dilator member is removed once the securing member is in place, the anchoring device of the invention is not bulky or cumbersome.

As noted above, the anchoring device of the invention may be used to secure any catheter. FIGS. 16–20 illustrate the anchoring device for use with an over-the-needle catheter. An over-the-needle catheter consists generally of a needle coupled to an extended stylet and a catheter cannula extending over the needle and the length of the stylet. In an over-the-needle catheter, the needle and catheter cannula are placed simultaneously, allowing the use of a smaller needle size, e.g., 3–4 gauges smaller, than a through-the-introducer type catheter where the catheter must enter through the opening created by the needle. In the over-the-needle catheter design, the outside diameter of the catheter is greater than the opening made by the needle, thus allowing a similar diameter catheter to be inserted with a smaller needle.

A problem associated with over-the-needle catheters is that it can be difficult to insert both the needle and the catheter cannula at the same time. Since the catheter moves freely over the needle and stylet, when the needle is inserted, the catheter may buckle or resist entry. One way to overcome this problem is through the use of deformable clamping wings which clamp or pinch the catheter and needle when the wings are folded together.

FIGS. 16 and 17 illustrate an embodiment of the invention wherein the securing member 410 includes deformable wings that, when compressed or folded, clamp or pinch the catheter and needle or stylet. FIG. 16 illustrates the securing member 410 with the wings in a down or unfolded position. FIG. 17 illustrates the securing member 410 with wings in a folded or clamping position on the catheter cannula 400 and the needle 440 coupled to the stylet 450. The anchoring device of this embodiment works similarly to that described above with reference to FIGS. 1–15 including a securing member portion 410 and a dilator member 420 to dilate the body portion of the securing member 410. This embodiment adds the additional feature that the wings are deformable such that the securing member 410 may also clamp, by applying additional compressive force, the catheter cannula/needle as the cannula and needle are placed in a patient. Window 430 illustrates that the cannula and needle are squeezed by the securing device when the wings 410 are folded to impart additional compressive force. In an unfolded state, a non-dilated securing member 410 fixedly engages the cannula 400 as described above.

FIGS. 18–20 illustrate a further embodiment of the invention, particularly useful with over-the-needle catheters. Dilator member 520 is forced into securing member 510 and dilates the tubular body portion of securing member 510 as described above with reference to FIGS. 4–8 and the accompanying text. Dilator member further extends beyond the securing member 510 and into the skin/body of the patient as shown in FIG. 19. In this manner, the dilator member 520 acts as an introducer allowing a smoother transition for placing the catheter cannula, e.g., the over-the-needle catheter, by freeing the passageway and eliminating any skin drag. FIG. 20 illustrates that once the catheter is properly placed, the dilator member 520 may be removed from the skin/body and the securing member 510 and, optionally, removed from the catheter completely by division.

In the preceding detailed description, the invention is described with reference to specific exemplary embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. An adjustable anchoring device to retain a catheter cannula, the anchoring device comprising:

a securing member with a body portion having an opening extending through said body portion, said opening with a first dimension to retain the catheter cannula at a desired location inside a patient by frictionally engaging said catheter cannula, and a second dimension that is larger than said first dimension such that said securing member can slidably move about the catheter cannula, a dilator member having a body with a forward end and an opening extending through said body portion larger than the outside dimension of the catheter cannula, wherein said forward end is adapted to detachably mate with said securing member through a portion of said opening of said securing member and to dilate said body portion of said securing member from having an opening with said first dimension to having an opening with said second dimension.

2. The anchoring device of claim 1, wherein said forward end of said dilator member includes a substantially tubular body portion having an opening extending through said dilator body portion wherein said diameter of said opening is greater than said outside diameter of said catheter cannula such that said dilator can slidably move about said catheter cannula, and wherein said tubular body of said securing member is dilated to have an opening with said second diameter by said body portion of said dilator.

3. The anchoring device of claim 2, wherein said body portion of said dilator member includes a tapered portion to assist said mating of said dilator member with said securing member.

4. The anchoring device of claim 2, wherein said tubular body portion of said dilator member is comprised of a durable material wherein said tubular body portion is adapted to be divided into two pieces.

5. An anchoring device to retain a catheter cannula, the anchoring device comprising:

a securing member with a body portion having an opening extending through said body portion, said opening with a first dimension adapted to retain said catheter cannula by frictionally engaging said catheter cannula and said body portion being dilatable to have an opening with a second dimension such that said securing member can slidably move about said catheter cannula, a dilator member with a forward end, said forward end of said dilator member having a body portion having an opening extending through said body portion wherein said diameter of said opening is greater than said outside diameter of said catheter cannula such that said dilator member can slidably move about said catheter cannula, said forward end of said dilator member adapted to detachably mate with said securing member through a portion of said opening of said securing member and to dilate said body portion of said securing member from having an opening with said first dimension to having an opening with said second dimension, and said body portion of said forward end of said dilator member having one of a scored and a sliced section substantially extending about said length of said body portion.

6. The anchoring device of claim 1, wherein said body portion of said securing member is comprised of a dilatable elastomeric material.

7. The anchoring device of claim 1, wherein said first dimension of said opening of said securing member is less than said outside diameter of said catheter cannula such that said securing member is adapted to retain said catheter cannula by compressively engaging said catheter cannula.

8. The anchoring device of claim 1, wherein said securing member further comprises a securing wing portion coupled to said body portion to secure said securing member to the exterior body of a patient.

9. The anchoring device of claim 8, wherein said securing wing portion is integrally formed with said body portion of said securing member.

10. The anchoring device of claim 1, wherein said body portion of said securing member comprises a substantially tubularly shaped portion.

11. The anchoring device of claim 10, wherein said tubular body portion of said securing member includes a curved portion.

12. The anchoring device of claim 1, wherein said body portion of said securing member comprises a substantially annularly shaped portion.

13. The anchoring device of claim 1, wherein said body portion of said securing member comprises a plurality of substantially annularly shaped portions.

14. The anchoring device of claim 1, wherein said body portion of said securing member comprises an arcuately-shaped portion.

15. The anchoring device of claim 1, wherein said body portion of said securing member comprises a plurality of substantially arcuately-shaped portions.

16. The anchoring device of claim 1, wherein said securing member comprises deformable securing wing portions having a first position and a second position, wherein in said first position and said opening in said body portion of said securing member having a second dimension, said anchoring device is adapted to frictionally engage said catheter cannula, and wherein in said second position said anchoring device can slidably move about said catheter cannula.

17. The anchoring device of claim 1, wherein said forward end of said dilator member is adapted to be advanced through a catheter opening in a patient.

18. A catheter kit comprising:

a catheter cannula having an outside dimension to be inserted into a patient; and an adjustable anchoring device including a securing member with a body portion having an opening extending through said body portion, said opening having a first dimension to retain said catheter cannula by frictionally engaging said catheter cannula and a second dimension that is larger than said first dimension such that said securing member can slidably move about said catheter cannula and a dilator member having a body portion with a forward end and an opening extending through said body portion and larger than said outside dimension of said catheter cannula, wherein said forward end is adapted to detachably mate with said securing member through a portion of said opening of said securing member and to dilate said body portion of said securing member from having an opening with said first dimension to having an opening with said second dimension.

19. The kit of claim 18, wherein said body portion of said securing member of said anchoring device is comprised of a dilatable elastomeric material.

20. The kit of claim 18, wherein said first dimension of said opening of said securing member of said anchoring device is less than said outside diameter of said catheter cannula such that said securing member is adapted to retain said catheter cannula by compressively engaging said catheter cannula.

21. The kit of claim 18, wherein said securing member of said anchoring device further comprises a securing wing portion coupled to said body portion to secure said securing member to the exterior body of a patient.

22. The kit of claim 21, wherein said securing wing portion is integrally formed with said body portion of said securing member.

23. The kit of claim 18, wherein said body portion of said securing member of said anchoring device comprises a substantially tubularly shaped portion.

24. The kit of claim 23, wherein said tubular body portion of said securing member includes a curved portion.

25. The kit of claim 18, wherein said body portion of said securing member of said anchoring device comprises a substantially annularly shaped portion.

26. The kit of claim 18, wherein said body portion of said securing member of said anchoring device comprises a plurality of substantially annularly shaped portions.

27. The kit of claim 18, wherein said body portion of said securing member of said anchoring device comprises an arcuately-shaped portion.

28. The kit of claim 18, wherein said body portion of said securing member of said anchoring device comprises a plurality of substantially arcuately-shaped portions.

29. The kit of claim 18, wherein said securing member of said anchoring device comprises deformable securing wing portions having a first position and a second position, wherein in said first position and said opening in said body portion of said securing member having a second dimension, said anchoring device is adapted to frictionally engage said catheter cannula, and wherein in said second position said anchoring device can slidably move about said catheter cannula.

30. The kit of claim 18, wherein said forward end of said dilator member of said anchoring device is adapted to be advanced through a catheter cannula opening in a patient.

31. The kit of claim 18, wherein said dilator member of said anchoring device is adapted to remain about said catheter once said catheter is placed in a patient.

32. A catheter kit comprising:

a catheter cannula to be inserted into a patient; and an adjustable anchoring device including a securing member with a body portion having an opening extending through said body portion; and a dilator member with a forward end, wherein said forward end of said dilator member is adapted to detachably mate with said securing member through a portion of said opening of said securing member and to dilate said body portion of said securing member from having an opening with a first dimension adapted to retain said catheter cannula by frictionally engaging said catheter cannula to having an opening with a second dimension such that said securing member can slidably move about said catheter cannula, wherein said forward end of said dilator member of said anchoring device includes a substantially tubular body portion having an opening extending through said dilator body portion wherein said diameter of said opening is greater than said outside diameter of said catheter cannula such that said dilator member can slidably move about said catheter cannula, and wherein said body of said securing member of said anchoring device is dilated to have an opening with said second diameter by said body portion of said dilator member.

33. The kit of claim 32, wherein said tubular body portion of said dilator member is comprised of a durable material wherein said tubular body portion is adapted to be divided into two pieces.

34. The kit of claim 33, wherein said tubular body portion has one of a scored and a sliced section substantially extending about said length of said tubular body portion.

* * * * *